United States Patent
Sofiienko et al.

(10) Patent No.: US 9,817,152 B2
(45) Date of Patent: Nov. 14, 2017

(54) METHODS AND MEANS FOR CREATING THREE-DIMENSIONAL BOREHOLE IMAGE DATA

(71) Applicant: Visuray Intech Ltd (BVI), Road Town, Tortola (VG)

(72) Inventors: Andrii Sofiienko, Randaberg (NO); David Ponce, Randaberg (NO); Ådne Voll, Stavanger (NO); Philip Teague, Houston, TX (US)

(73) Assignee: VISURAY INTECH LTD (BVI), Tortola (VG)

( * ) Notice: Subject to any disclaimer, the term of this patent is extended or adjusted under 35 U.S.C. 154(b) by 0 days.

(21) Appl. No.: 15/065,345

(22) Filed: Mar. 9, 2016

(65) Prior Publication Data
US 2016/0187528 A1    Jun. 30, 2016

Related U.S. Application Data

(63) Continuation of application No. 14/231,368, filed on Mar. 31, 2014, now abandoned.
(Continued)

(51) Int. Cl.
*G01V 5/08* (2006.01)
*G01V 5/12* (2006.01)
(Continued)

(52) U.S. Cl.
CPC ............. *G01V 5/08* (2013.01); *G01N 23/203* (2013.01); *G01N 23/204* (2013.01); *G01V 5/125* (2013.01)

(58) Field of Classification Search
None
See application file for complete search history.

(56) References Cited

U.S. PATENT DOCUMENTS 3,321,627 A    5/1967    Tittle
3,564,251 A    2/1971    Youmans
(Continued)

FOREIGN PATENT DOCUMENTS

WO    2009079134 A2    6/2009

OTHER PUBLICATIONS

U.S. Appl. No. 14/231,368.
Office Action dated Sep. 9, 2015 in corresponding U.S. Appl. No. 14/231,368.

*Primary Examiner* — Edwin Gunberg
(74) *Attorney, Agent, or Firm* — Raymond R. Ferrera; Adams and Reese LLP

(57) ABSTRACT

A method of creating three-dimensional borehole data is provided, including illuminating a borehole using collimated beams of electromagnetic radiation; rotating the collimated beams in a sweep of at least 360 degrees; detecting backscattered electromagnetic radiation returned from surfaces of associated illumination planes using electromagnetic radiation sensors; converting detected radiation into a corresponding set of volume image data; analyzing the volume image data using computational visualization processing techniques; and creating a three-dimensional image representative of the volume data. Imaging methodologies include a complete, radial conic-shaped surface while the imaging system remains stationary; a plurality of scans performed while longitudinally moving the imaging system a distance d through the borehole between image capture operations; and a plurality of scans performed while longitudinally moving the imaging system a distance d, where d is a distance less than or equal to the collimated beam thickness, so that adjacent scans partially overlap.

38 Claims, 5 Drawing Sheets

Related U.S. Application Data

(60) Provisional application No. 61/919,376, filed on Dec. 20, 2013.

(51) Int. Cl.
*G01N 23/203* (2006.01)
*G01N 23/204* (2006.01)

(56) References Cited

U.S. PATENT DOCUMENTS

| | | | |
|---|---|---|---|
| 3,567,935 A * | 3/1971 | Nagel | G01V 5/107 250/264 |
| 3,976,879 A | 8/1976 | Turcotte | |
| 4,433,240 A | 2/1984 | Seeman | |
| 4,464,569 A | 8/1984 | Flaum | |
| 4,661,700 A * | 4/1987 | Holenka | G01V 5/125 250/256 |
| 4,705,944 A | 11/1987 | Coope | |
| 4,879,463 A * | 11/1989 | Wraight | G01V 5/12 250/254 |
| 4,883,956 A | 11/1989 | Melcher et al. | |
| 5,081,611 A | 1/1992 | Hornby | |
| 5,326,970 A | 7/1994 | Bayless | |
| 5,729,582 A * | 3/1998 | Ham | G01N 23/20066 378/86 |
| 6,078,867 A | 6/2000 | Plumb et al. | |
| 6,725,161 B1 | 4/2004 | Hillis et al. | |
| 6,876,721 B2 | 4/2005 | Siddiqui | |
| 7,634,059 B2 | 12/2009 | Wraight | |
| 7,675,029 B2 | 3/2010 | Ramstad et al. | |
| 7,705,294 B2 | 4/2010 | Ramstad et al. | |
| 8,138,471 B1 | 3/2012 | Shedlock et al. | |
| 8,481,919 B2 | 7/2013 | Teague | |
| 2003/0223620 A1* | 12/2003 | Anxionnaz | G01V 1/50 382/109 |
| 2013/0009049 A1 | 1/2013 | Smaardyk et al. | |
| 2013/0261974 A1 | 10/2013 | Stewart et al. | |

* cited by examiner

METHODS AND MEANS FOR CREATING THREE-DIMENSIONAL BOREHOLE IMAGE DATA

FIELD OF THE INVENTION

The present invention relates generally to creation and interpretation of three-dimensional borehole image data, and in a particular though non-limiting embodiment to methods and means of measuring and characterizing structures disposed within or immediately surrounding the borehole of a water, oil or gas well. Also disclosed are means for recreating imaged structures as three-dimensional data images using a software-enabled data reconstruction method comprising data detected through backscattered radiation collection and processing.

BACKGROUND

Since water, oil and gas wells are generally lined with one or more metal casing strings adhered to the formation surrounding the wellbore by hardened cement, it is advantageous to perform quality inspections of the materials used to construct the well in order to ensure long-term operability of the well. Such materials include, but are not limited to, the geological formations themselves, the casings and the cements.

Such quality inspections include, but are not limited to, measuring the thickness or density to discover any texture characteristics and structural defects such as mechanical flaws, inhomogeneities in the materials, incomplete or missing materials, damage caused by geological or subsurface movement, time varying modification of the strata behind the casings due to fluid migration, and/or corrosion of materials.

Furthermore, wells can be fractured so that they release trapped hydrocarbons into the borehole and can be produced at the surface; in this case the reservoir rock is fractured by the operator by pumping specially designed fluids into the well at pressures high enough to make fissile subsurface rocks crack along fault lines. The effectiveness of this approach is critically dependent upon the fracture aperture and the lateral extent of the fracture. A means to geometrically characterize the fracture system, as well as a measurement of in situ stresses in the formation, are therefore important in predicting and measuring the propagation and extent of the fracture into the reservoir.

There are currently several non-destructive methods of well inspection available to operators, viz.:

1. Mechanical means, such as in-bore multi-fingered calipers;
2. In-bore optical camera methods;
3. Near-bore ultrasonic imaging methods;
4. Far-bore ultrasonic imaging methods;
5. Sonic logging methods to determine cement bond quality;
6. Electromagnetic methods to evaluate corrosion and well integrity; and
7. Electrical imaging methods used to determine the borehole shape, and to create a resistivity map of the borehole wall that can identify geological features as well as fractures in the reservoir rock.

The mechanical means, such as the caliper, and the optical camera only produce information pertaining to the physical inner surface of the inner-most casing of the well, and are therefore incapable of offering operators information regarding the status of materials outside of the inner surface, such as the cement bond or volume.

Near-bore ultrasonic imaging methods, such as rotating single ultrasonic transducers, rely upon a method of emitting ultrasonic pulses in the frequency range of 100 to 800 kHz, and then receiving and measuring waveforms that have been reflected from the inner and outer surface of the inner-most casing.

The rate of decay of the waveforms indicates the quality of the cement bond to the outer surface of the inner-most casing, and can detect features as small as 2-3 centimeters in size. The resonant frequency of the casing provides information on the wall thickness of the casing. However, this ultrasonic method cannot be used to determine the structure of materials outside of the cement-casing interface.

Far-bore ultrasonic imaging methods rely on multiple panoramic ultrasonic transducers and imagers that compare received waveforms reflected from surfaces or interfaces of rapid density changes to inversion models of the wellbore structures created prior to the operation. In order to solve the time-of-flight inversion needed to resolve the ultrasonic data into image data (which contains radial distance data), the operator must create three-dimensional models of the wellbore apparatus prior to performing a data-collection operation. Thus, the operator effectively needs to know what an anomaly looks like and where it is located in advance in order to obtain a satisfactory image of the anomaly. Moreover, since the method is based upon reflected waveforms obtained from density-change interfaces, it is incapable of producing meaningful data regarding the nature of the cement bond or any cement volume discrepancies.

When a sonic logging method is used, a wire line tool is run in the borehole to detect how well the cement is bonded to the casing and formation via a principle based on resonance. Casing that is not bound has a higher resonant vibration than casing that is bound, which causes the energy from the sonic signal to be transferred to the formation. While this effect serves to detect a poor cement bond for normal cement, it fails to distinguish between an acceptable bond and a poor bond when low acoustic impedance cements are used, for example as is usually the case in deep water wells. In such instances, all casing appears to be poorly bonded.

Another disadvantage of the method is that the measurement is averaged azimuthally around the borehole and therefore cannot identify the orientation of any breach in the cement bond. Finally, it should be noted that this method can detect bond anomalies only on the order of 25 cm or greater along the longitudinal borehole axis, while vital breaches in the cement bond with smaller dimensions often occur.

There are two common electromagnetic methods used to evaluate the integrity of the tubing or casing. First, an eddy current device can be used to measure the presence of pits and holes in the inner wall of a casing. In the best practice of this method, the eddy-current measurement is used in conjunction with a flux-leakage measurement to determine casing corrosion, the latter being sensitive to defects on both the inner and outer walls. A transmitter coil produces a high frequency, alternating current magnetic field that induces eddy currents in the casing wall. These currents generate their own magnetic field, which induces a signal in two closely-spaced receiver coils. In smooth casing, these signals are the same, but if the inner wall is pitted, the signals are different.

Second, in a borehole within which a tubing or casing is installed, a low frequency electromagnetic wave propagation directly affected by the thickness of metal of the tubular in which it lies is transmitted and sensed within a borehole by a logging tool. The transmitted electromagnetic wave travels radially through the well-fluid before permeating through the tubing wall to the area outside.

The wave then propagates along the length of the tubing before re-entering the pipe, at which point it is measured by an array of detector antennae within the logging tool. As the wave propagates through the metal wall of the tubular its velocity and amplitude are reduced, however, the wave is unaffected by well fluid or formation properties. The transmitter-detector transit time and the amplitude of the electromagnetic wave are measured by the tool, and in turn are used to derive wall thickness.

These two techniques are often combined in a single borehole tool so that the measurements are made in the same run in the well. While this method provides an average wall thickness or detects anomalies on the inner and outer surfaces for the first tubing or casing in a well, it cannot make any measurements of a second casing or tubing in the same well. Moreover, while multiple pads deployed to detect anomalies provide azimuthal information regarding the presence of pits or holes in the casing, full circumferential coverage of the tubing or casing wall cannot be achieved.

Finally, in open boreholes assessed prior to being cased, an electrical current can be injected into the reservoir rock by a logging tool and sensed by a plurality of electrodes; in this event the electrodes are typically arranged to form an array disposed substantially perpendicular to the axis of the tool and deployed on mechanical pads pressed against the borehole wall. As the tool moves up the borehole wall, the sensed current in each of the plurality of electrodes varies in proportion to the local conductivity of the reservoir rock.

A current reading obtained from each sensing electrode is then displayed as an image spanning the circumference of the borehole as the tool moves vertically within the hole. Since the borehole fluid is more conductive than the rock formation, any fluid which fills a fracture that intersects the borehole results in a relatively higher current, with the current increasing in value in proportion to the aperture of the fracture, thus evaluating the effectiveness of the fracture in enhancing the production of hydrocarbons from the reservoir rock. In addition to the measurement of the currents, the tool measures the dimensions of the borehole in two perpendicular directions, thereby indicating the direction and magnitude of the elongation of the borehole and enabling a derivation of the in situ stress in the reservoir. This final measurement may be combined with the fracture evaluation to model the extent of the fracture in the reservoir rock.

While the measurement is made on multiple arms and pads attached to the tool, it does not provide full circumferential coverage of the borehole wall. Moreover, the determination of the aperture relies on accurate measurements of the rock resistivity and the resistivity of the borehole fluid. Finally, the aperture determination fails to provide meaningful information regarding how the aperture varies in magnitude as well as direction as it extends into the formation and therefore provides limited information about the fracture network.

In sum, there are no currently known technologies available to operators to permit detailed three-dimensional imaging of wellbore casings and the structures within and surrounding the wellbore, which offer information obtained from the inner surface or the inner-most casing, through multiple casings and annuli to a volume including the cement and geological formations. There is similarly a lack of technologies that permit the detailed three-dimensional imaging of the near-well environment just outside the borehole.

The invention comprises a method to measure the discrete structures within and immediately surrounding a borehole and to recreate said structures as a three-dimensional representation through mathematical reconstructions of x-ray backscattered volume imaging. These methods are further embodied by means that may be used to practice the method for use in a water, oil or gas well.

In conventional, non-destructive three-dimensional imaging methods based upon x-ray technology, an operator acquires x-ray attenuation data in wedges through a sample by moving an x-ray source and electronic imaging device arranged on opposite sides of a sample around the outside of the sample. Mathematical processing, typically Radon transform or computational processing, via various algorithms, is applied to each data slice to create a three-dimensional reconstruction of the sample. The resulting reconstructions are typically displayed as two-dimensional slice images, though the underlying data actually represent volumetric properties of the sample. Various visualization techniques that better represent the three-dimensional quality of the data are becoming more prevalent.

In addition to x-ray computed tomography scans (CT), tomograms are currently derived using several other physical phenomena such as gamma rays in single-photon emission computed tomography scans (SPECT), radio-waves in magnetic resonance imaging (MRI), electrons in transmission electron microscopy (TEM), and electron-positron annihilation in positron emission tomography (PET). However, all tomograms are derived from an outside-in perspective, wherein the radiation source and/or imaging device are located on the outside or around the sample to be imaged.

The prior art teaches a variety of techniques that use x-rays or other radiant energy to inspect or obtain information about the structures within or surrounding the borehole of a water, oil or gas well, though none teach any type of inside-out volume imaging technique as described and claimed later in this application.

For example, U.S. Pat. No. 3,564,251 to Youmans discloses the use of a radially scanning collimated x-ray beam used to produce an attenuated signal at a detector for the purpose of producing a spiral-formed log of the inside of a casing or borehole surface immediately surrounding the tool.

U.S. Pat. No. 7,675,029 to Teague et al. provides an apparatus that permits the measurement of x-ray backscattered photons from any horizontal surface inside of a borehole that refers to two-dimensional imaging techniques.

U.S. Pat. No. 7,634,059 to Wraight discloses an apparatus that may be used to measure two-dimensional x-ray images of the inner surface inside of a borehole, but lacks the ability to look inside of the borehole in a radial direction.

U.S. Pat. No. 8,481,919 to Teague teaches a method of producing high-energy photon radiation in a borehole without the use of radioactive isotopes, and further describes rotating collimators disposed around a fixed source installed internally within the apparatus, but does not have rotatable solid-state detectors with collimators. It further teaches the use of conical and radially symmetrical anode arrangements that permit the production of panoramic x-ray radiation.

US 2013/0009049 by Smaardyk discloses an apparatus that allows measurement of backscattered x-rays from the inner layers of a borehole, but lacks the ability to reconstruct a three-dimensional representation.

U.S. Pat. No. 8,138,471 to Shedlock discloses a scanning-beam apparatus based on an x-ray source, a rotatable x-ray beam collimator, and solid-state radiation detectors that enable the imaging of only the inner surfaces of borehole casings and pipelines.

U.S. Pat. No. 5,326,970 to Bayless discloses a tool that measures backscattered x-rays from inner surfaces of a borehole casing with the x-ray source being based on a linear accelerator.

U.S. Pat. No. 7,705,294 to Teague et al. teaches an apparatus that measures backscattered x-rays from the inner layers of a borehole in selected radial directions with the missing segment data being populated through movement of the apparatus through the borehole. The apparatus permits generation of data for a two-dimensional reconstruction of the well or borehole, but does not disclose the geometry needed for illuminating an x-ray beam so as to permit discrimination of the depth from which the backscattered photons originated, rather it only discloses the direction.

U.S. Pat. No. 5,081,611 to Hornby discloses a method of back projection to determine acoustic physical parameters of the earth formation longitudinally along the borehole using a single ultrasonic transducer and a number of receivers, which are typically distributed along the primary axis of the tool.

U.S. Pat. No. 6,725,161 to Hillis et al. discloses a method of placing a transmitter in a borehole, and a receiver on the surface of the earth, or perhaps a receiver in a borehole and a transmitter on the surface of the earth, in order to determine structural information regarding the geological materials between the transmitter and receiver.

U.S. Pat. No. 6,876,721 to Siddiqui discloses a method of correlating information derived from a core-sample with information obtained from a borehole density log. The core-sample information is derived from a CT scan of the core-sample, whereby the x-ray source and detectors are located on the outside of the sample and thereby configured as an outside-looking-in arrangement. Various types of information derived from the CT scan, e.g., bulk density, is then compared to and correlated with the log information.

U.S. Pat. No. 4,464,569 to Flaum discloses a method of determining the elemental composition of earth formations surrounding a well borehole using detected neutron capture gamma radiation emanating from the earth formation following neutron irradiation of the earth formation by a neutron spectroscopy logging tool.

U.S. Pat. No. 4,433,240 to Seeman discloses a borehole logging tool that detects natural radiation obtained from the rock of the formation and logs that information so that it may be represented in an intensity versus depth plot format.

U.S. Pat. No. 3,976,879 to Turcotte discloses a borehole logging tool that detects and records backscattered radiation obtained from the formation surrounding the borehole by means of a pulsed electromagnetic energy or photon source, so that characteristic information can be represented in an intensity versus depth plot format.

U.S. Pat. No. 4,883,956 to Manente et al. discloses an apparatus and method for investigation of subsurface earth formations using an apparatus adapted for movement through a borehole. Depending upon the formation characteristic or characteristics to be measured, the apparatus may also include a natural or artificial radiation source for irradiating the formations with penetrating radiation such as gamma rays, x-rays or neutrons. The light produced by a scintillator in response to detected radiation is then used to generate a signal representative of at least one characteristic of the radiation, and this signal is recorded.

U.S. Pat. No. 6,078,867 to Plumb et al. discloses a method for generating a three-dimensional graphical representation of a borehole by, for example, receiving caliper data relating to the borehole, generating a three-dimensional wire mesh model of the borehole from the caliper data, and color mapping the three-dimensional wire mesh model from the caliper data based on either borehole form, rugosity and/or lithology.

U.S. Pat. No. 3,321,627 to Tittle discloses a system having collimated detectors and collimated gamma-ray sources used to determine the density of a formation outside of a borehole so that it can be represented in a density versus depth plot format.

There is, therefore, a long-felt need that remains unmet despite many prior unsuccessful attempts to achieve a volume image derived from an inside-out perspective, wherein the radiation source and imaging device are both located within the sample, in a manner that overcomes the various shortcomings of the prior art.

SUMMARY

A method of creating three-dimensional borehole data is provided, including at least the steps of illuminating a borehole using one or more collimated beams of electromagnetic radiation; rotating the one or more collimated beams in a sweep of at least 360 degrees; detecting backscattered electromagnetic radiation returned from one or more surfaces of associated illumination planes using one or more electromagnetic radiation sensors; converting detected radiation into a corresponding set of volume image data; and analyzing the volume image data using computational visualization processing techniques; and creating a three-dimensional image representative of the volume data.

Various imaging methodologies include at least a complete, radial conic-shaped surface while the imaging system remains stationary; a plurality of scans performed while longitudinally moving the imaging system a distance d through the borehole between image capture operations; and a plurality of scans performed longitudinally while moving the imaging system a distance d through the borehole, where d is a distance less than or equal to the collimated beam thickness so that portions of adjacent scans at least partially overlap.

Various systems, structures and means suitable for performing these methods are also disclosed.

DETAILED DESCRIPTION OF SEVERAL EXAMPLE EMBODIMENTS

Figure 1:
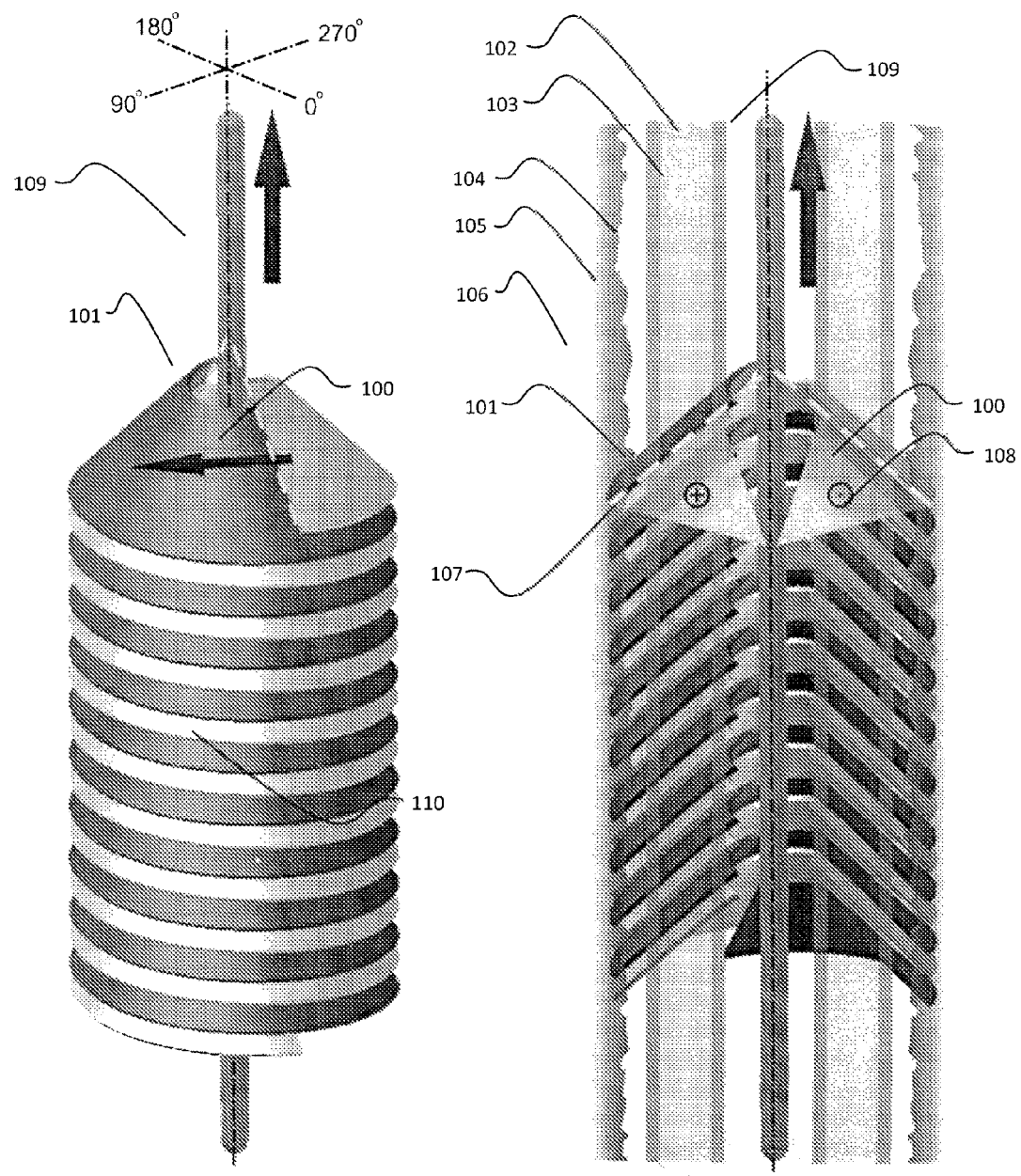
FIG. 1 depicts a first embodiment comprising two revolving collimated beams of x-rays radially offset by 180 degrees radially. The resulting illuminated areas of the well materials, such as an inner casing, annulus, outer casing, cement and formation are imaged within the imaging system by detector arrays, which are collimated to ensure that they only receive backscattered radiation from the areas of the illumination planes. As the imaging system moves through the borehole the imaged surfaces are represented by a double helical ribbon.

There are no previously known technologies available on the market capable of providing an operator with non-destructive means for determining the composition or status of materials and constructions located behind the inner casing of a borehole, nor of the regions surrounding the borehole, with any significant detail.

The invention described and claimed herein therefore comprises a method and means for permitting an operator to determine the current status of mechanical flaws, inhomogeneity in the materials, incomplete or missing materials, damage caused by geological or subsurface movement, time variant modification of the strata behind the casings attributable to fluid migration, and/or corrosion of materials. The objects of the invention are achieved by creating accurate volume image data, which are then analyzed in detail using computational visualization techniques.

In addition, when used in an open borehole the method penults the operator to detect and geometrically characterize fractures intersecting the open borehole, while at the same time providing a complete description of the borehole geometry, thereby enabling a meaningful estimate of in-situ stresses in the earth. This combination allows the operator to fully characterize the fracture apertures, particularly their extent and variation thereof as they extend into the formation, thereby allowing for a more accurate determination of the improvement in the permeability of the formation due to the fracture.

By employing the method the operator would gain access to a full three-dimensional reconstruction of the structures within and around the borehole. This volume data is then viewed as a longitudinal two-dimensional section from the centreline of the borehole outward in stepped offsets of the operator's choosing, ranging out to the edge of the imaged volume created by the method. Similarly, the volume image data can be represented as transverse two-dimensional sections so that cross-sectional views of regions of interest within the borehole may be analysed in detail.

Further reprocessing will identify contiguous volumetric regions within the three-dimensional volume image data, thereby enabling the operator to visually deconstruct, reduce or remove the visibility of certain sections of volumetric data to isolate key features within the borehole construction. The operator can visually remove all volume elements from their computationally rendered view of the image data so as to leave only the cement layer, for example, or so as to identify areas of under-sized or missing cement, etc.

The principle of this method and means is to use one or more beams of ionizing radiation to illuminate a region of borehole and its surroundings in such a manner that a detector system can be arranged to effectively record a two-dimensional image of the illuminated plane. When the imaging system is moved longitudinally through the borehole, additional planes are illuminated and imaged. Longitudinal stacking of the transverse two-dimensional images enables processing of the stacked data such that three-dimensional volume data of the borehole surroundings may be created. The resultant volume data set is then analysed to provide complete tomographic datasets of the borehole surroundings, its geometrical makeup, and materials.

An example method of creating three-dimensional borehole data comprises illuminating a borehole using one or more collimated beams of electromagnetic radiation; rotating the one or more collimated beams in a sweep of at least 360 degrees; detecting backscattered electromagnetic radiation returned from one or more surfaces of associated illumination planes using one or more electromagnetic radiation sensors; converting detected radiation into a corresponding set of volume image data; and analyzing the volume image data using computational visualization processing techniques; and creating a three-dimensional image representative of the volume data.

With reference now to associated FIG. 1, an example embodiment is depicted in which the volume around a borehole is illuminated by two revolving collimated beams 100, 101 of electromagnetic radiation, which are radially offset by 180 degrees and tilted away from the transverse plane of the borehole by an angle of between 0 and 90 degrees.

In another embodiment, the beams of radiation may be composed of x-rays, gamma-rays, neutrons or other spectrum of electromagnetic radiation. The resulting illuminated areas of the well materials, such as an inner casing 102, annulus 103, outer casing 104, cement 105 and formation 106 are imaged within the imaging system 109 using one or more radiation detector arrays.

In a further embodiment the system includes a plurality of apertures to ensure that the detectors only receive radiation from the direction of the illuminated material planes 107, 108. The radiation received can be the result of any associated backscatter radiation interactions such as a Rayleigh scatter, a Compton scatter, x-ray fluorescence, elastic or inelastic neutron scattering interactions, neutron absorption within the material planes, etc. As the imaging system 109 moves longitudinally through the borehole, the simultaneous action of the pair of revolving beams causes the imaged regions to remain contiguous.

In a still further embodiment, contiguous, swept imaging regions are diagrammatically represented by a double helical ribbon 110. In each subsequent iteration in the same radial direction (as indicated by the coordinate rose in FIG. 1), the imaged plane contains imaging information regarding specific material regions in the borehole surroundings from the previous pass of the radiation beam, but from a different imaging angle compared to the collimation of the detector arrays. The ability to collect image data of the same borehole surrounding materials from different angles permits algorithmic computational analysis of the two-dimensional image ribbons necessary to create three-dimensional volume image data.

In one embodiment, iterative reconstruction techniques are used to reconstruct the three-dimensional volume image data. Due to the ray paths passing through well fluids and possibly several material layers, significant attenuation will occur along the paths and thus noise statistics will be relatively poor. For example, iterative algorithm approaches can be used to provide decreased sensitivity to noise and the capability of reconstructing an optimal image in the case of incomplete or missing data or when image data is not distributed uniformly in angle. However, other methods of algorithmic reconstruction may be used to transform the two-dimensional image ribbons into three-dimensional volume image data as will occur to the ordinarily skilled artisan.

Figure 2:
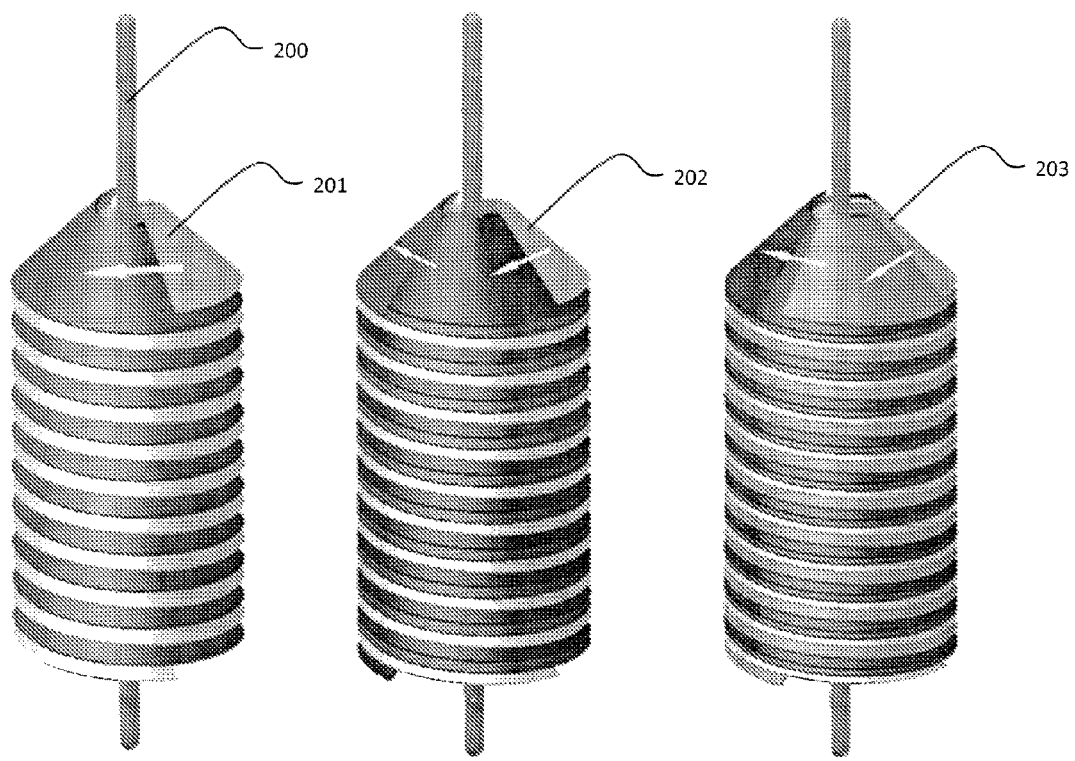
FIG. 2 depicts plural embodiments of the configuration disclosed in FIG. 1, viz., embodiments comprising two revolving collimated beams of radiation radially offset by 180 degrees that illuminate the volume around the borehole, thereby creating imaging planes represented by a double helical image-plane ribbon; three revolving collimated beams offset by 120 degrees, thereby producing a triple helical image-plane ribbon; four revolving collimated beams offset by 90 degrees, thereby producing a quadruple helical image-plane ribbon; or any number 'n' of revolving collimated beams offset by 360/n degrees that will produce an n-helical image plane ribbon.

In the example embodiment depicted in FIG. 2, the imaging system 200 is configured such that two revolving collimated beams of x-rays or other electromagnetic radiation are radially offset by 180 degrees and illuminate a discreet volume around the borehole, thereby creating illuminated planes represented by a double helical image-plane ribbon 201.

However, alternative configurations are within the scope of this disclosure, such as three revolving collimated beams offset by 120 degrees, thereby producing a triple helical image-plane ribbon 202; four revolving collimated beams offset by 90 degrees, thereby producing a quadruple helical image-plane ribbon 203; or more generally any number 'n' of revolving collimated beams offset by 360/n degrees, which will produce an n-helical image plane ribbon, etc.

A further embodiment would permit a complete conical beam of radiation whereby a conical imaging plane would be imaged by a single 360 degree collimated aperture. In a still further embodiment of the imaging system 200 beams of neutrons or gamma-rays as a replacement for x-rays will also be effective.

In yet another embodiment, the method admits to the imaging of complete, radial conic-shaped surfaces while the imaging system is stationary. This method further comprises longitudinally moving the imaging system a relatively short distance through the borehole in between image capture operations. The form of the resulting dataset will be that of a non-contiguous set of two-dimensional surfaces, which would be stacked in a three-dimensional space. Alternately, the dataset can be contiguous if the movement in each step is selected as less than the beam thickness, so that portions of subsequent scans partly overlapped.

Figure 3:
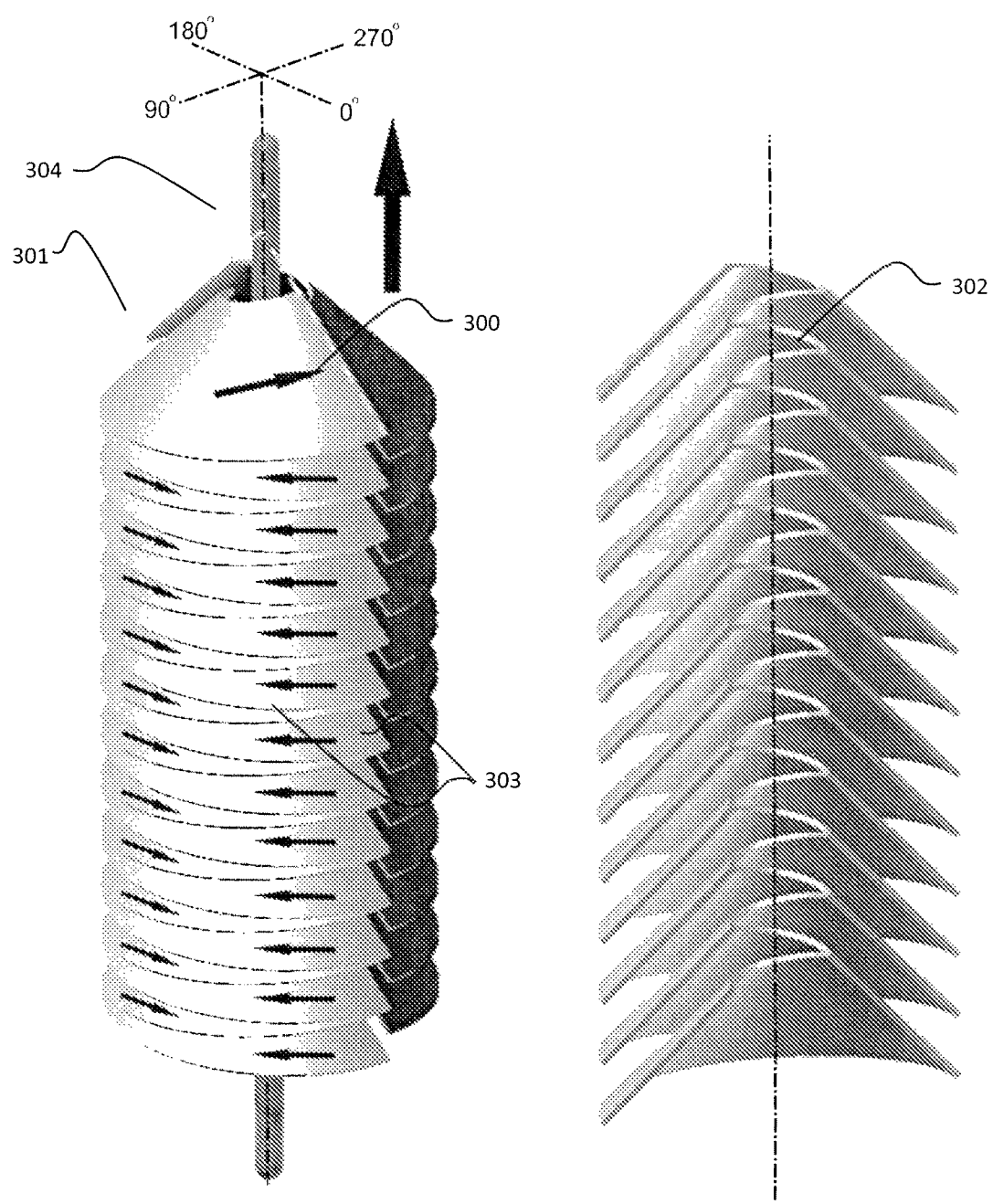
FIG. 3 depicts an embodiment in which the volume around the borehole is illuminated by two reciprocating collimated beams of radiation radially offset by 180 degrees. As the imaging system moves through the borehole, the imaged surfaces are represented by a pair of continuous, stacked oscillating half-conic ribbons, the form of which is illustrated to the right. Configurations such as three reciprocating collimated beams offset by 120 degrees thereby producing a triplet of continuous stacked oscillating third-conic ribbons, or any number 'n' of reciprocating collimated beams offset by 360/n degrees to produce n-continuous stacked oscillating 1/n-conic ribbons, are also within the scope of this disclosure.

In the example embodiment depicted in FIG. 3, the volume around the borehole is illuminated by two reciprocating collimated beams 300, 301 of radiation radially offset by 180 degrees. As the imaging system 304 moves longitudinally through the borehole, the imaged surfaces are represented by a pair of continuous, stacked oscillating half-conic ribbons 302, the general form of which is illustrated to the right of FIG. 3.

Other example configurations, such as three reciprocating collimated beams offset by 120 degrees, will produce a triplet of continuous stacked oscillating third-conic ribbons, and more generally, any number 'n' of reciprocating collimated beams offset by 360/n degrees will produce n-continuous stacked oscillating 1/n-conic ribbons. This approach has the benefit of reducing the overall mechanical complexity of any imaging system means or apparatus to which the method would be applied, as the imaging system would only need to be actuated in a reciprocating angle of less than 180 degrees at any one time, making electrical connections simpler and less prone to failure.

Figure 4:
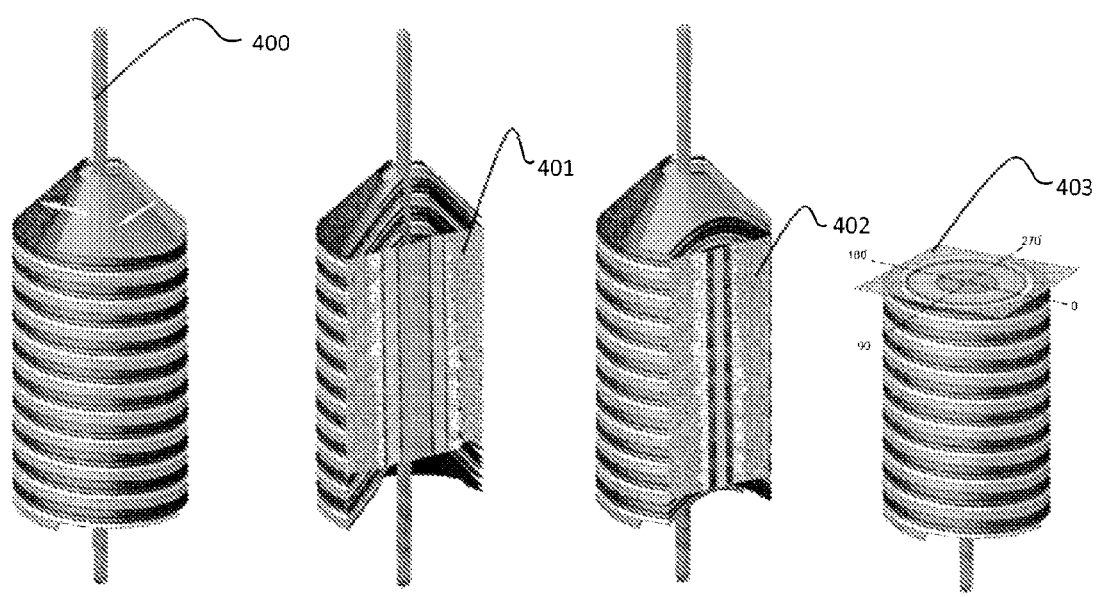
FIG. 4 depicts an embodiment in which a quadruple helical image-plane ribbon produced by the imaging device is used to illustrate how captured volume image data can be represented to an operator as longitudinal two-dimensional sectional views, measured relative to a centreline of the borehole out in stepped offsets to the edge of the imaged volume. In an alternative embodiment, the volume image data is represented as transverse two-dimensional sections.

Either during or after the collection of the image data, the collected volume data is reprocessed in order to enable an operator to view the borehole surroundings and geometrical construction as longitudinal two-dimensional sectional views measured from the centreline of the borehole out in a series of stepped offsets of the operator's choosing, ranging out to the edge of the imaged volume (see, for example, the example embodiment depicted in FIG. 4 at elements 401, 402).

In an alternative embodiment, the volume image data is represented as transverse two-dimensional sections (see FIG. 4, element 403), so that cross-sectional views of regions of interest within the borehole are acquired for detailed analysis. Further reprocessing of contiguous volumetric regions detected within the three-dimensional volume image data will enable an operator to visually deconstruct, reduce or remove the visibility of certain sections of volumetric data in order to isolate key features within the borehole construction. The operator then visually removes all volume elements from the computationally rendered view of the image data, leaving only the cement layer, for example, so to be able to identify areas of under-sized or missing cement.

Figure 5:
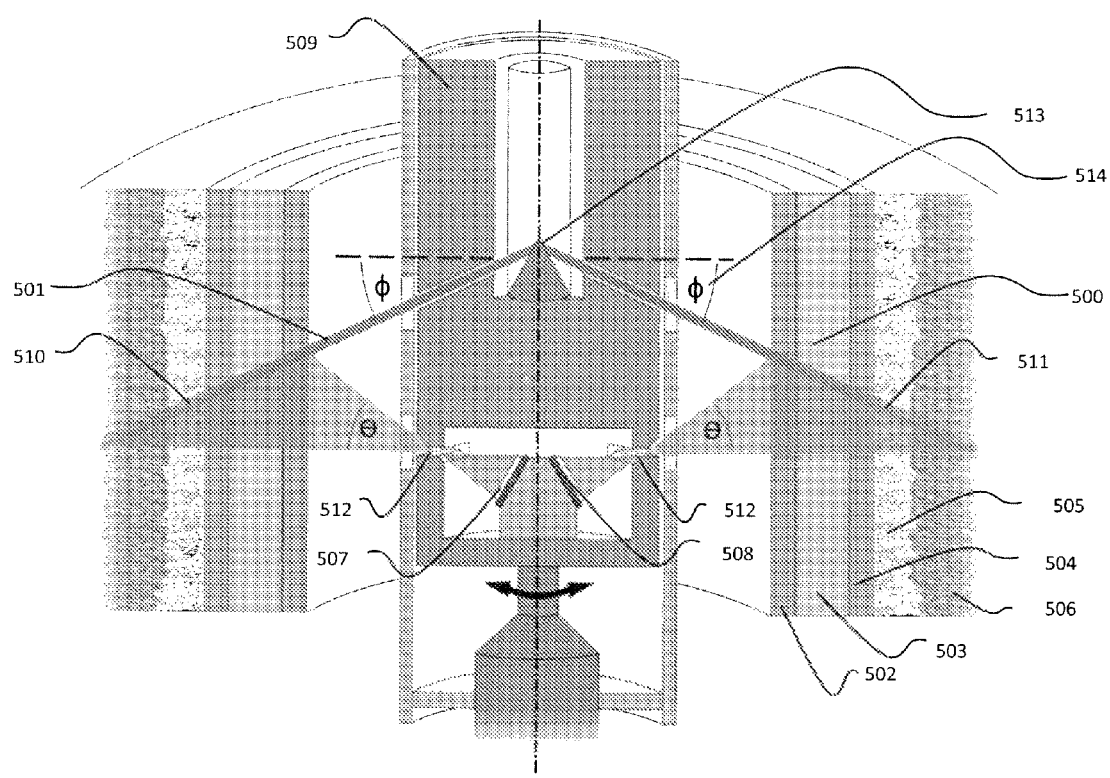
FIG. 5 depicts an embodiment comprising a volume around the borehole that is illuminated by two revolving collimated beams of radiation radially offset by 180 degrees and tilted away from the transverse plane by an angle Φ. The resulting illuminated areas of the well materials, such as an inner casing, annulus, outer casing, cement and formation are imaged by detector arrays within the rotating radiation shield enclosure. In the depicted embodiment the shield includes an aperture to ensure that the detector arrays only receive backscattered radiation from the areas of the illumination planes. In a further embodiment the apertures image a region prescribed by an optimum collimation angle θ.

In the example embodiment depicted in FIG. 5, the volume around the borehole is illuminated by two revolving collimated beams 500, 501 of x-rays emanating from an x-ray source 513. In this example, the beams are radially offset by 180 degrees and tilted away from the transverse plane of the borehole by an angle 4, which can comprise any angle between 0 and 90 degrees. The radiation beam is collimated by a plurality of high aspect holes 514 formed in the rotating radiation shield enclosure 509 with a collimation ratio of at least 2:1, whereby the length of the collimator is closely approximate to twice that of the diameter of the collimator orifice. However, ordinarily skilled artisans will recognize that a plurality of low aspect collimator holes can also be employed depending on desired operational parameters.

The resulting illuminated areas of the well materials, such as an inner casing 502, annulus 503, outer casing 504, cement 505 and formation 506 are imaged by a plurality of detector arrays 507, 508 disposed within the rotating radiation shielded enclosure 509. The shield includes a plurality of apertures 512 so as to ensure that the detectors only receive backscattered radiation from a specified area of the illumination planes 510, 511. That area is prescribed by the collimation angle θ, which determines the geometry of the imaging collimators 512. In one example embodiment, the detector array comprises a multi-strip detector, or instead a quasi-one-dimensional array, so that it is segmented in the longitudinal direction (though not necessarily perpendicularly). When combined with an appropriate imaging collimator, the detection system admits to a representative depth discrimination of the backscattered x-rays, thereby achieving a three-dimensional reconstruction.

In a further embodiment, detector systems sensitive to discriminating the energy of scattered radiation are used to achieve one or more of a plurality of interpretive methods, including (though not limited to) x-ray fluorescence, so that elemental composition of the scattering medium is achieved. The fluorescent characteristics of specific elements, viz., bismuth or barium, etc., are then identified within the imaged volume. This technique admits to the identification and removal of data collected as a result of multiple scattering events or other undesired portions of the energy spectrum.

In a still further embodiment, the x-ray source 513 and the detector arrays 507, 508 are mechanically fixed within the radiation shielded enclosure 509 such that they rotate together with the radiation shielded enclosure 509. In this manner, the radiation shielded enclosure 509 effectively rotates within the pressure housing that encompassed the entire imaging system. However, any means admitting to production of a rotating or oscillating plurality of collimated beams can be employed with equal efficacy.

The foregoing specification is provided for illustrative purposes only, and is not intended to describe all possible aspects of the present invention. Moreover, while the invention has been shown and described in detail with respect to several exemplary embodiments, those of skill in the pertinent arts will appreciate that minor changes to the description and various other modifications, omissions and additions may be made without departing from the scope thereof.

The invention claimed is:

1. A method of creating three-dimensional borehole data, said method comprising:
   illuminating a borehole using a collimated beam of electromagnetic radiation originating from a tool centrally disposed within said borehole, wherein said beam comprises radial, axial and azimuthal components;
   rotating said collimated beam in a sweep of at least 360 degrees;
   detecting backscattered electromagnetic radiation returned from a surface of an associated illumination plane using an associated electromagnetic radiation sensor;
   converting detected radiation into a corresponding set of volume image data;
   analyzing said volume image data using a computational visualization processing technique; and
      creating a three-dimensional image representative of said volume image data.

2. The method of claim 1, further comprising illuminating a borehole using two collimated beams of electromagnetic radiation radially separated by approximately 180 degrees, thereby creating a three-dimensional data image in the shape of a double helix.

3. The method of claim 1, further comprising illuminating a borehole using three collimated beams of electromagnetic radiation radially separated by approximately 120 degrees, thereby creating a resulting three-dimensional data image in the shape of a triple helix.

4. The method of claim 1, further comprising illuminating a borehole using four collimated beams of electromagnetic radiation radially separated by approximately 90 degrees, thereby creating a resulting three-dimensional data image in the shape of a quadruple helix.

5. The method of claim 1, further comprising illuminating a borehole using n collimated beams of electromagnetic radiation radially separated by approximately 360/n degrees, thereby creating a resulting three-dimensional data image of an n-shaped helix.

6. The method of claim 1, further comprising tilting the transverse plane of said collimated beam by more than zero degrees and less than or equal to approximately 90 degrees.

7. The method of claim 5, further comprising tilting the transverse plane of said collimated beam by more than zero degrees and less than or equal to approximately 90 degrees.

8. The method of claim 1, further comprising illuminating a borehole using a collimated x-ray beam.

9. The method of claim 1, further comprising illuminating a borehole using a collimated gamma-ray beam.

10. The method of claim 1, further comprising illuminating a borehole using a collimated neutron beam.

11. The method of claim 1, wherein said detecting backscattered electromagnetic radiation returned from a surface of an associated illumination plane further comprises detecting an associated backscatter radiation interaction.

12. The method of claim 1, wherein said detecting backscattered electromagnetic radiation returned from a surface of an associated illumination plane further comprises detecting at least one of a Rayleigh scatter, a Compton scatter, and an x-ray fluorescence event.

13. The method of claim 1, wherein said detecting backscattered electromagnetic radiation returned from a surface of an associated illumination plane further comprises detecting at least one of an elastic neutron scattering, an inelastic neutron scattering, and a neutron absorption interaction.

14. The method of claim 1, wherein said analyzing said volume image data using computational visualization processing techniques and said creating a three-dimensional image representative of said volume image data further comprises applying one or more iterative data processing reconstruction techniques to said volume image data.

15. The method of claim 14, wherein said applying one or more iterative data processing reconstruction techniques further comprises applying one or iterative algorithms.

16. The method of claim 14, further comprising applying one or more iterative data processing reconstruction techniques to said volume image data so that signal data attenuation is reduced.

17. The method of claim 16, wherein said applying one or more iterative data processing reconstruction techniques to said volume image data so that signal data attenuation is reduced further comprises reducing signal noise data.

18. The method of claim 1, further comprising using an electromagnetic radiation sensor to detect the elemental composition of an associated scattering medium.

19. The method of claim 1, wherein said method further comprises one or more of:
   imaging a complete, radial conic-shaped surface while the imaging system remains stationary;
   longitudinally moving the imaging system a distance d through the borehole between image capture operation, thereby resulting in a plurality of non-contiguous datasets of two-dimensional images that are stacked using computational visualization processing techniques, and then creating an integrated three-dimensional image representative of the stacked volume image data; and
   longitudinally moving the imaging system a distance d through the borehole, where d is a distance less than or equal to the collimated beam thickness, so that portions of adjacent scans at least partially overlap.

20. A system for creating three-dimensional borehole data, said system comprising:
- means for illuminating a borehole using a collimated beam of electromagnetic radiation originating from a tool centrally disposed within said borehole, wherein said beam comprises radial, axial and azimuthal components;
- means for rotating said collimated beam in a sweep of at least 360 degrees;
- means for detecting backscattered electromagnetic radiation returned from a surface of an associated illumination plane using an associated electromagnetic radiation sensor;
- means for converting detected radiation into a corresponding set of volume image data;
- means for analyzing said volume image data using a computational visualization processing technique; and
- means for creating a three-dimensional image representative of said volume image data.

21. The system of claim 20, further comprising means for illuminating a borehole using two collimated beams of electromagnetic radiation radially separated by approximately 180 degrees, thereby creating a three-dimensional data image in the shape of a double helix.

22. The system of claim 20, further comprising means for illuminating a borehole using three collimated beams of electromagnetic radiation radially separated by approximately 120 degrees, thereby creating a resulting three-dimensional data image in the shape of a triple helix.

23. The system of claim 20, further comprising means for illuminating a borehole using four collimated beams of electromagnetic radiation radially separated by approximately 90 degrees, thereby creating a resulting three-dimensional data image in the shape of a quadruple helix.

24. The system of claim 20, further comprising means for illuminating a borehole using n collimated beams of electromagnetic radiation radially separated by approximately 360/n degrees, thereby creating a resulting three-dimensional data image of an n-shaped helix.

25. The system of claim 20, further comprising means for tilting the transverse plane of said collimated beam by more than zero degrees and less than or equal to approximately 90 degrees.

26. The system of claim 24, further comprising means for tilting the transverse plane of said collimated beam by more than zero degrees and more than or equal to approximately 90 degrees.

27. The system of claim 20, further comprising means for illuminating a borehole using a collimated x-ray beam.

28. The system of claim 20, further comprising means for illuminating a borehole using a collimated gamma-ray beam.

29. The system of claim 20, further comprising means for illuminating a borehole using a collimated neutron beam.

30. The system of claim 20, wherein said means for detecting backscattered electromagnetic radiation returned from a surface of an associated illumination plane further comprises means for detecting an associated backscatter radiation interaction.

31. The system of claim 20, wherein said means for detecting backscattered electromagnetic radiation returned from a surface of an associated illumination plane further comprises means for detecting at least one of a Rayleigh scatter, a Compton scatter, and an x-ray fluorescence event.

32. The system of claim 20, wherein said means for detecting backscattered electromagnetic radiation returned from a surface of an associated illumination plane further comprises means for detecting at least one of an elastic neutron scattering, an inelastic neutron scattering, and a neutron absorption interaction.

33. The system of claim 20, wherein said means for analyzing said volume image data using a computational visualization processing technique and said means for creating a three-dimensional image representative of said volume image data further comprises means for applying one or more iterative data processing reconstruction techniques to said volume image data.

34. The system of claim 33, wherein said means for applying one or more iterative data processing reconstruction techniques further comprises means for applying one or iterative algorithms.

35. The system of claim 33, further comprising means for applying one or more iterative data processing reconstruction techniques to said volume image data so that signal data attenuation is reduced.

36. The system of claim 35, wherein said means for applying one or more iterative data processing reconstruction techniques to said volume image data so that signal data attenuation is reduced further comprises means for reducing signal noise data.

37. The system of claim 20, further comprising means for using an electromagnetic radiation sensor to detect the elemental composition of an associated scattering medium.

38. The system of claim 20, wherein said system further comprises one or more of:
- means for imaging a complete, radial conic-shaped surface while the imaging system remains stationary;
- means for longitudinally moving the imaging system a distance d through the borehole between image capture operations, thereby resulting in a plurality of non-contiguous datasets of two-dimensional images that are stacked using a computational visualization processing technique, and then creating an integrated three-dimensional image representative of the stacked volume image data; and
- means for longitudinally moving the imaging system a distance d through the borehole, where d is a distance less than or equal to the collimated beam thickness, so that portions of adjacent scans at least partially overlap.

* * * * *